US007015198B1

(12) United States Patent
Orentreich et al.

(10) Patent No.: US 7,015,198 B1
(45) Date of Patent: Mar. 21, 2006

(54) MATERIALS FOR SOFT TISSUE AUGMENTATION AND METHODS OF MAKING AND USING SAME

(75) Inventors: Norman Orentreich, New York, NY (US); Rozlyn A. Krajcik, Poughquag, NY (US)

(73) Assignee: Orentreich Foundation for the Advancement of Science, Inc., New York, NY (US)

( * ) Notice: Subject to any disclaimer, the term of this patent is extended or adjusted under 35 U.S.C. 154(b) by 0 days.

(21) Appl. No.: 09/309,689

(22) Filed: May 11, 1999

(51) Int. Cl.
*A61K 38/00* (2006.01)
*A61K 38/16* (2006.01)
*A61K 35/14* (2006.01)

(52) U.S. Cl. ................. 514/21; 514/2; 514/8; 530/380; 424/529; 424/530

(58) Field of Classification Search ................. 514/21, 514/8, 2; 530/380; 424/529, 530
See application file for complete search history.

(56) References Cited

U.S. PATENT DOCUMENTS

| | | | |
|---|---|---|---|
| 3,152,976 A | 10/1964 | Kuntz | 530/356 |
| 4,006,220 A | 2/1977 | Gottlieb | 424/101 |
| 4,046,871 A * | 9/1977 | Reckel | 435/7.25 |
| 4,061,731 A | 12/1977 | Gottlieb | 424/101 |
| 4,404,970 A | 9/1983 | Sawyer | 128/325 |
| 4,969,912 A | 11/1990 | Kelman et al. | 623/66 |
| 5,147,514 A | 9/1992 | Mechanic | 204/157.68 |
| 5,188,834 A | 2/1993 | Grimm et al. | 424/422 |
| 5,328,955 A | 7/1994 | Rhee et al. | 525/54.1 |
| 5,332,802 A | 7/1994 | Kelman et al. | 530/356 |
| 5,527,856 A | 6/1996 | Rhee et al. | 525/54.1 |
| 5,550,187 A | 8/1996 | Rhee et al. | 525/54.1 |
| 5,628,781 A | 5/1997 | Williams et al. | 623/1 |
| 5,630,842 A | 5/1997 | Brodniewicz | 623/8 |
| 5,733,545 A | 3/1998 | Hood, III | 424/93.72 |
| 5,804,428 A | 9/1998 | Edwardson et al. | 435/212 |
| 6,020,181 A * | 2/2000 | Bini | 435/226 |

FOREIGN PATENT DOCUMENTS

GB 1013577 12/1965

OTHER PUBLICATIONS

Coleman III, et al (eds. *Skin Resurfacing*, pp. 217-234, 1998.*
Pollack (Dermatol. Surg. Oncol., vol. 16. No. 10, pp. 957-961, Oct. 1990.*
Grabarek et al., *Analytical Biochem.* vol. 185, pp. 131-135, 1990.*
Wang et al, *J. of Parenteral Drug Assoc.* vol. 34, No. 6, pp 452-462, Nov.-Dec. 1980.*
Wong, *Chemistry of Protein Conjugation and Cross-Linking*, pp. 39-40 and 195-207, 1991.*
Coleman III, et al., ([eds.] Skin Resurfacing, pp. 217-234, 1998.*
Pollack, J. Dermatol. Surg. Oncol., vol. 16, No. 10, pp. 957-961, 1990.*
Grabarek et al., Analytical Biochemistry, vol. 185, pp. 131-135, 1990.*
Wong, Chemistry of Protein Conjugation and Cross-linking, pp. 39-40 and 195-207, 1991.*
Wang et al., Juornal of the Parenteral Drug Association, vol. 34, No. 6, pp. 452-462, Nov.-Dec. 1980.*
Alster, et al., "New Options for Soft Tissue", *Skin & Aging*, pp. 32-34, 36, (Jul. 1998).
Asken, Saul, "Microliposuction and Autologous Fat Transplantation for Aesthetic Enhancement of the Aging Face", *J. Dermatol. Surg. Oncol.*, vol. 16(10), pp. 965-972, (Oct. 1990).
Balazs, E.A., et al., "Hyaluronan, Its Crosslinked Derivative—Hylan—And Their Medical Applications", *Cellulosics Utilization: Research and Rewards in Cellulosics, Proceedings of Nisshinbo International Conference on Cellulosics Utilization in the Near Future*, pp. 233-241, (1989).
Balazs, E., et al., "Hyaluronan, Hylans and Their Medical Applications", *The Biotechnology Report*, pp. 159-160, (1993).
Biomatrix Product Information, "Hylaform®", http://www.biomatrix.com/page5.htm, (Jun. 15, 1998).
Boshart, J.M., "Physician Marketing Correspondence," Collagen Corporation (Mar. 30, 1982).
Burges, L.P.A., et al., "Injectable Collagen", *Facial Plastic Surgery*, vol. 8, No. 3, pp. 176-182 (Jul. 1992).
Cheung, et al., "Mechanism of Crosslinking of Proteins by Glutaraldehyde IV: In Vitro and In Vivo Stability of a Crosslinked Collagen Matrix", *Connective Tissue Research*, vol. 25, pp. 27-34, (1990).
Coleman III, et al., (eds.), *Skin Resurfacing*, pp. 217-234, (1998).
Collagenesis Corporate Profile (1995) (3 pages).
Collagenesis Press Release (Feb. 6, 1998) (3 pages).
Davidsohn, I., et al., *Clinical Diagnosis By Laboratory Methods*, 15th Edition, Chapter 4, pp. 100-104, (1974).
Dermalogen™ Product Information, Collagenesis, Inc. (4 pages).

(Continued)

*Primary Examiner*—Jon Weber
*Assistant Examiner*—Abdel A. Mohamed
(74) *Attorney, Agent, or Firm*—Akin Gump Strauss Hauer & Feld, LLP

(57) ABSTRACT

Materials for soft tissue augmentation in mammals are prepared by cross-linking blood plasma proteins, preferably with a zero-length cross-linking agent. The cross-linked blood plasma proteins can be dialyzed and autoclaved. Such materials are non-antigenic, exhibit decreased allergic response, and have increased longevity with respect to proteolytic attack from natural proteases. The appearance and/or feel of soft tissue defects and/or imperfections in skin can be improved by injecting such materials into an intradermal compartment of a patient's skin.

19 Claims, 3 Drawing Sheets

OTHER PUBLICATIONS

Elson, M.L., "Soft tissue augmentation: Update 1997", *J. Clinical Dermatology*, pp. 25-30, (Winter, 1998).

Elson, M.L., "Soft Tissue Augmentation of Periorbital Fine Lines and the Orbital Groove with Zyderm-1 and Fine-Gauge Needles",*J. Dermatol. Surg. Oncol.,* vol. 18, pp. 779, 781, (1992).

Elson, M.L., "Clinical Use of Collagen Injectable Materials", *Cosmetic Surgery Update*, pp. 15-18.

Feder, B.J., "Biotechnology Unit Has Product to Sell", *New York Times*, Business Section, pp. 1, 36, ( Mar. 27, 1982).

Feinendegen, et al., "Autologous Fat Injection for Soft Tissue Augmentation in the Face: A Safe Procedure?" *Aesthetic Plastic Surgery*, vol. 22, pp. 163-167, (1998).

Golcman, et al., "Fat Transplantation and Facial Contour", *Amer. J. of Cosmetic Surgery*, vol. 15, No. 1, pp. 41-44, (1998).

Grabarek, et al., "Zero-Length Crosslinking Procedure with the Use of Active Esters", *Analytical Biochemistry*, vol. 185, pp. 131-135, (1990).

"Hylan Gel Shows Promise for Soft Tissue Augmentation", *Dermatology Times*, p. 11, (Mar. 1994).

Kaufman, M.J., "New Soft-Tissue Augmentation Substance Has Great 'Potential", *Cosmetic Dermatology*, pp. 44-45, (Feb. 1993).

Larsen, N.E., et al., "Hylan gel biomaterial: Dermal and immunologic compatibility", *Journal of Biomedical Materials Research*, vol. 27, pp. 1129-1134, (1993).

McPherson, et al., "The preparation and physicochemical characterization of an injectable form of reconstituted, glutaraldehyde cross-linked, bovine corium collagen", *J. of Biomedical Materials Research*, vol. 20, pp. 79-92, (1986).

Moyer, Paula, "New Human Collagen Products May Produce Long-lasting Results", *Dermatology Times*, pp. 36-37, (Mar. 1998).

Moyer, Paula, "Autologous Human Collagen: Nonallergenic, but Less Predictable", *Dermatology Times*, pp. 94-95, (Feb. 1998).

Nidecker, Anna, "Cultured Fibroblasts Provide New Collagen Source", *Skin & Allergy News*, p. 43, (Mar. 1998).

Nimni, M.E., et al., "Chemically Modified Collagen: A Natural Biomaterial for Tissue Replacement", *Journal of Biomedical Materials Research*, vol. 21, pp. 741-771, (1987).

Olenius, M., The First Clinical Study Using a New Biodegradable Implant for the Treatment of Lips, Wrinkles, and Folds, *Aesth. Plast. Surg.*, vol. 22, pp. 97-101 (1998).

Parkinson, T.M., "Zyderm® Collagen Implant Safety Notice" Collagen Corporation (Mar. 3, 1983).

Putnam, F. (ed.), "Fractionation and Isolation of Purified Components by Precipitation Methods", *The Plasma Proteins*, vol. 1, Chp. 2, pp 9-50, (1960).

Pollack, Sheldon V., "Silicone, Fibrel, and Collagen Implantation for Facial Lines and Wrinkles", *J. Dermatol. Surg. Oncol.*, vol. 16(10), pp. 957-961, (Oct. 1990).

Stegman, S.J., et al., "A Light and Electron Microscopic Evaluation of Zyderm Collagen and Zyplast Implants in Aging Human Facial Skin", *Archives of Dermatology*, vol. 123, pp. 1644-1649, (Dec. 1987).

Swanson, N., et al., "Clarification on the Approved Uses of Injectable Collagen", *American Society for Dermatologic Surgery Newsletter*, vol. 2, No. 2, pp. 1-2 (May 1992).

Swinehart, James M., "Dermal Pocket Grafting: Implants of Dermis, Fat, and 'Autologous Collagen' for Permanent Correction of Cutaneous Depressions", *International Journal of Aesthetic and Restorative Surgery*, vol. 2, No. 1, pp. 43-52, (1994).

Timkovich, R., "Detection of the Stable Addition of Carbodiimide to Proteins",*Analytical Biochemistry*, vol. 79, 135-143 (1977).

Udenfriend, S., et al., "Fluorescamine: A Reagent for Assay of Amino Acids, Peptides, Proteins, and Primary Amines in the Picomole Range", *Science*, vol. 178, pp. 871-872, (Nov. 1972).

Wang, Y.J., et al., "Review of Excipients and pH's for Parenteral Products Used in the United States", *Journal of the Parenteral Drug Association*, vol. 34, No. 6, pp. 452-462, (Nov.-Dec. 1980).

Warden, J., "Blood supplies to be treated to reduce CJD risk", BMJ, 317:232, http://www.bmj.comkgi/content/full/317/7153/232/a (Jul. 27, 1998).

West, T.B., et al., "Autologous Human Collagen and Dermal Fibroblasts for Soft Tissue Augmentation", *American Society for Dermatologic Surgery, Inc.*, vol. 24, pp. 510-512, (1998).

Wilchek, M., et al., "A Highly Sensitive Colorimetric Method for the Determination of Carbodiimides"*Analytical Biochemistry*, vol. 114, pp. 419-421, (1981).

Wong, S.S., *Chemistry of Protein Conjugation and Cross-Linking*, pp. 39-40, 195-207 (1991).

Zyderm® 1&2/Zyplast® Product Information, Collagen Corporation (1997) (4 pages).

"Zyderm® Collagen Explained", Collagen Corporation, (1983) (3 pages).

"The Collagen Answer for Each Indication", Collagen Corp. (1 page).

Zyderm® Collagen Implant-Package Insert (3 pages).

Zyderm® 1&2/Zyplast® Product Information, Collagen Corporation (1998) (1 page).

Zyderm™ Product Information, Collagen Corporation (1981) (4 pages).

Zyderm™ Product Information, Collagen Corporation (Nov. 1981) (8 pages).

"3% Have Positive Skin Test Response to Implantable Bovine Collagen", *Skin & Allergy News* pp. 1, 3 (1982).

Fibrel® (gelatin matrix implant), Physician Package Insert, Distributed by Serono Laboratories, Inc., Apr., 1988.

* cited by examiner

MATERIALS FOR SOFT TISSUE AUGMENTATION AND METHODS OF MAKING AND USING SAME

BACKGROUND OF THE INVENTION

Soft tissue augmentation is a general term that collectively refers to methods which can be used to diminish the visibility of surface defects in skin, usually including the injection or implantation of some material into the skin of the patient. Injections and implantations can be located at varying depths below the epidermis, including intradermal and subcutaneous (hereinafter generally referred to as "dermal") depths, depending on the type of defect being treated, the desired effect and material used. Defects such as lines, wrinkles, scars, and the like can be substantially reduced, and in some cases can be made completely unnoticeable, at least temporarily, by such methods.

Soft tissue augmentation can be accomplished in a variety of ways. Two of the more common ways of augmenting soft tissue include the dermal insertion of semi-solid or solid implants of biocompatible materials and the dermal injection of biocompatible materials which may be in the form of a gel or a viscous liquid.

Many substances of varying chemical composition and derivation have been proposed and used as injectable materials for soft tissue augmentation. Materials which have been used in the long history of soft tissue augmentation include silicone products, paraffins, and autologous fat materials. Injectable materials for soft tissue augmentation, which currently seem to be the most widely used, are those which include collagen or are collagen-based. Collagen generally refers to a wide variety of fibrous proteins found in the skin, muscles, tendons, cartilage and bones of animals. Collagen, which usually contains a large amount of proline and hydroxyproline amino acid residues, exists in many triple-helix forms having slightly different physical properties.

There are many factors to be considered when evaluating an injectable material for soft tissue augmentation. These factors fall roughly into four categories which include medical properties, aesthetic properties, practicality and economic considerations. Among the medical properties which a material for soft tissue augmentation should ideally possess are: non-antigenicity, treatment longevity, and stability against migration. Thus, the materials should not cause any reactions in the patient's body, such as erythema, ulceration, inflammation, necrosis, hypo- or hyper-pigmentation, edema, granulomas and/or infection. The materials should cause minimal pain upon injection and should require minimal recuperation time. Aesthetically, the materials should have a natural look and feel to them once inserted into the body. A material which possesses some or all of the preferable medical and aesthetic qualities, should also be practically useful in that a physician can inject it through fine gauge needles with relative ease and withdraw the injection if necessary. Other practical considerations include the shelf life of the material, the storage conditions that the material requires, and the need, if any, for pre-injection preparation. Of course, less pre-injection preparation is preferred. Finally, the overall cost of the material should be considered.

Silicone materials can often be difficult to properly inject for the purposes of soft tissue augmentation.

Autologous fat injections, as well as paraffin injections, have long been known and studied. These materials also have disadvantages. Fat injections can in some circumstances be dangerous and are also very unpredictable with respect to results and treatment longevity. Fat injected into facial lines and wrinkles can cause loss of vision (amaurosis) and even embolism in some patients. Paraffin injections, which are not biocompatible, can result in chronic inflammation and granulomas. Furthermore, some varying portion of a fat injection is usually readily absorbed by the body. Thus, the overall effect of an injected amount of fat is difficult to predict.

Within the last ten to twenty years or so, bovine collagen and, more recently, autologous collagen have become widely used as injectable materials for soft tissue augmentation. However, bovine collagen products can cause allergic responses in patients injected with such materials. It is common to subject a patient to one and sometimes two skin tests using a bovine collagen product as an indicator of potential allergic reaction. Some patients who exhibit negative test results may subsequently develop an allergic reaction, despite such precautionary measures. Autologous collagen obtained from the patient's own body, usually from the patient's skin, and heterologous human collagen obtained from human cadavers have been proposed and implemented as materials for soft tissue augmentation as well. While autologous collagen has reduced the occurrence of allergic responses in some patients, this material also has disadvantages. Autologous collagen is generally produced using the patient's own skin as a starting material. Thus, the starting material is generally obtained by surgical excision of the patient's skin.

Another material which has been proposed for soft tissue augmentation is a gel which contains a cross-linked derivative of a hyaluronic acid. Hyaluronic acid is a high molecular weight polymer having acetylglycosamine and glucuronic acid as alternating units. Hyaluronic acid gels have an advantage over other prior art injectable materials in that they are composed of a polysaccharide which generally produces no adverse immunological effect in the patient. Thus, the adverse reactions are avoided for the most part, as with autologous collagen, but the use of the patient's own skin is avoided. Unfortunately, hyaluronic acid gels suffer from some of the same disadvantages as other prior art materials, particularly decreased longevity due to poor resistance to natural proteases within the patient's body. In general, prior art soft tissue augmentation materials are short-lived and require frequent repetitive injections to maintain skin defect correction levels.

Other gel materials which have been proposed and used for soft tissue augmentation are blood derived gels which are obtainable by withdrawing a patient's blood, combining blood proteins with ascorbic acid (vitamin C) and heat gelling the mixture. While these materials are relatively easy to obtain and cause little, if any, adverse reaction in a patient, they too suffer from a short-lifespan upon injection.

Many different approaches have been taken to increase the longevity of soft tissue augmentation materials by attempting to increase the material's resistance to proteolytic cleavage. Attempts to increase the resistance of prior art injectable materials have generally focused on chemical modification of the materials. Injectable materials containing collagen have been treated with chemical modifiers, such as acylating agents and esterifying agents, in an attempt to increase their proteolytic cleavage resistance. The additional cross-linking of collagen materials and hyaluronic acid has also been suggested for purposes including increasing viscosity and potentially increasing the material's resistance to proteolytic cleavage. Methods which have been proposed for cross-linking collagen materials include thermal, chemical, and irradiation methods. However, the cross-linking of these materials has not resulted in a superior product which is appreciably better in resistance to proteolytic attack by natural enzymes. At any rate, prior art injectable materials for soft tissue augmentation have often failed to satisfy many of the desired characteristics sought in such a material.

Therefore, there still exists a need in the art for safe, non-antigenic, non-irritating, longer-lasting and aesthetically-pleasing injectable materials for soft tissue augmentation which are relatively easy to obtain and/or manufacture.

BRIEF SUMMARY OF THE INVENTION

It has been found according to the invention that blood plasma proteins can be cross-inked to form materials which are easily injected, surprisingly resistant to proteolytic cleavage, non-antigenic, and aesthetically pleasing when used for soft tissue augmentation. These materials are significantly more stable with respect to attack by natural proteases than other injectable materials. Furthermore, it has been found that the materials of the present invention can be purified and sterilized providing even greater resistance to proteolytic attack.

According to the present invention, an injectable material for soft tissue augmentation in mammals comprises cross-linked, blood plasma proteins. It is preferable that the blood plasma proteins are cross-linked with a zero-length cross-linking agent and that the cross-linked proteins are optionally purified and/or sterilized. It is also preferred that the blood plasma proteins are obtained from an autologous blood sample.

Also, according to the present invention, a method of preparing an injectable material for soft tissue augmentation of a mammal comprises the steps of (a) providing a protein portion of a blood plasma sample and (b) cross-linking the protein portion to form a cross-linked blood plasma protein portion which is the injectable material. In accordance with a preferred embodiment of the present invention, the protein portion can be cross-linked with a zero-length cross-linking agent, and the method may additionally include subjecting the cross-linked blood plasma protein product to dialysis and autoclaving.

Furthermore, according to the present invention, a method of augmenting a soft tissue defect in a skin area of a mammal comprises injecting a material comprising a cross-linked, blood plasma protein into an intradermal compartment of the skin of the mammal.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited by the embodiment(s) used to obtain the data shown in the drawings. In the drawings.

DETAILED DESCRIPTION OF THE INVENTION

Figure 1:
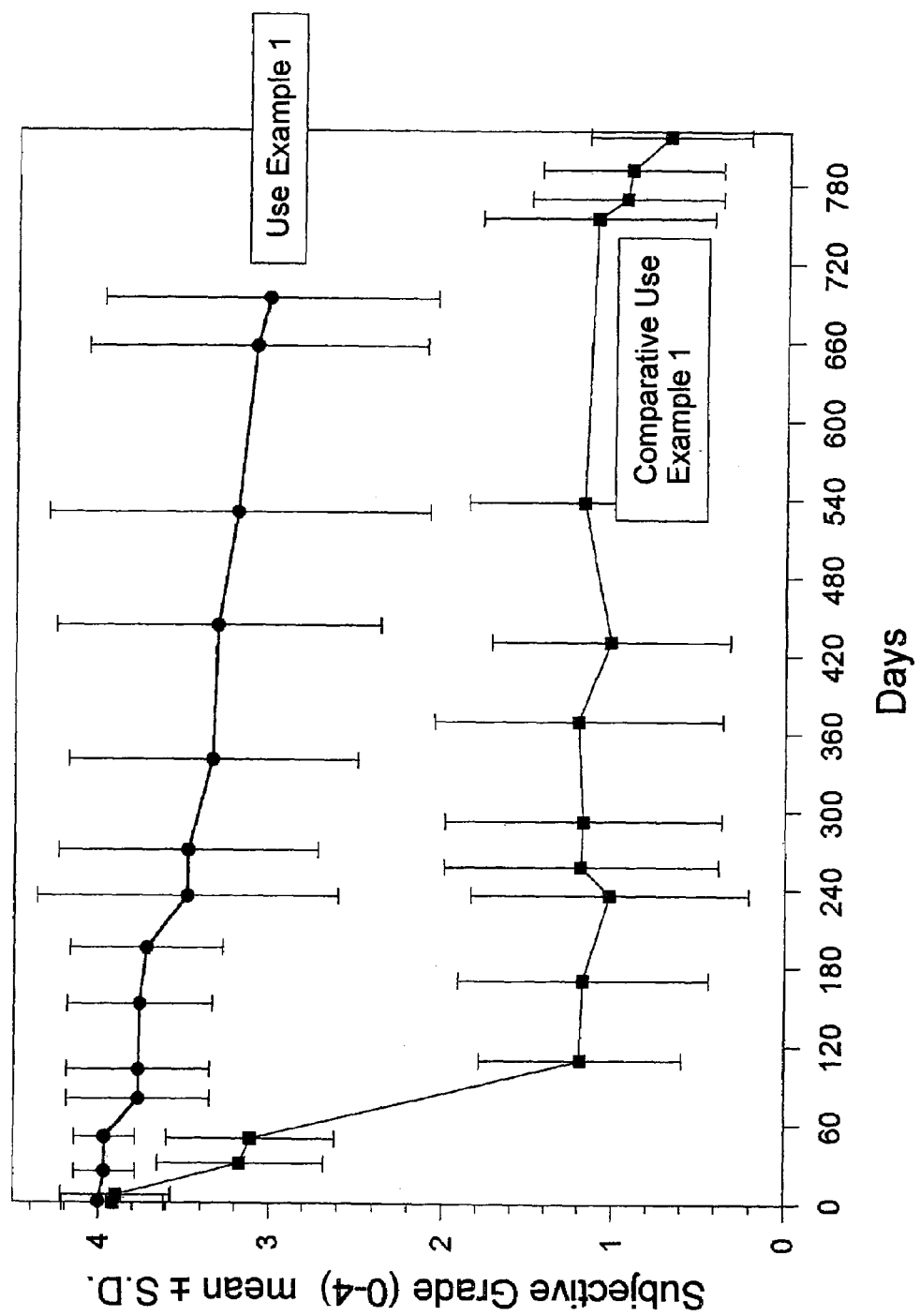
FIG. 1 is a graphical representation over time as measured in days of the subjective effect of in vivo proteolytic degradation and phagocytosis (biodegradation) of injectable materials prepared in accordance with Preparation Example 1 and Comparative Preparation Example 1, as used in Use Example 1 and Comparative Use Example 1.

The present invention, while generally applicable to all mammals, will be described with particular reference to humans.

Injectable materials for soft tissue augmentation in accordance with the present invention comprise cross-linked, blood plasma proteins. The blood plasma proteins are generally obtained from blood plasma which may be autologous or heterologous. Thus, the blood plasma can be obtained from blood which is taken directly from the patient or it may be taken from pooled blood. Blood may be drawn from a patient using standard laboratory procedures, such as, for example, the method disclosed by Davidsohn and Nelson in *Clinical Diagnosis by Laboratory Methods*, Chapter 4, 15th ed. (1974). Generally, it is not critical how blood is withdrawn or obtained, nor is it critical how the blood plasma is separated from the whole blood. Any medically- or clinically-acceptable method by which blood can be drawn or otherwise obtained, and any medically- or clinically-acceptable method of plasma separation can be used in accordance with the present invention.

Blood taken from the patient or from other donors should be collected in a tube or vial which does not contain ethylene diamine tetraacetic acid ("EDTA") as the anticoagulant or any other amine-containing agents which may adversely affect the efficiency of the cross-linking agent. Preferably, a collection vessel will contain an ACD ("acid citrate dextrose") solution as the anticoagulant, in an amount of about 1.5 mL. Heparin is also an acceptable anticoagulant. An ACD solution generally contains trisodium citrate, citric acid and dextrose. For example, collection tubes having glycerated stoppers and an 8.5 mL draw capacity and which contain 1.5 mL of a solution containing 22 g/L of trisodium citrate, 8 g/L citric acid and 24.5 g/L of dextrose, are suitable for use in collecting blood from the patient or other donor, in accordance with the present invention. Two containers, each containing 8.5 mL of blood normally yield an appropriate amount of blood plasma, which is approximately 10 mL.

A preferred method by which the plasma can be separated from the blood is centrifugation. For example, collection tubes containing whole blood can be centrifuged at about 1500 rpm for approximately 10 minutes, at any suitable temperature including room temperature. The plasma can be removed from the collection tubes using a sterilized pipette or any other suitable means. The plasma can be used immediately in accordance with the present invention or it may be stored.

The plasma may be stored, and remain substantially unaffected by the storage with respect to its use in accordance with the present invention, for a periods of up to about two weeks at a temperature of about 4° C., or indefinitely at a temperature of about −20° C. or less. Plasma stored for a long period of time should preferably be re-centrifuged to remove any coagulated material or other debris which tends to settle out.

Heterologous pooled human blood plasma, such as that which may be obtained from the American Red Cross, could be used in accordance with the present invention as well. If heterologous blood from other donors, or pooled human blood plasma is used, it is preferable to ensure the quality of the blood or plasma by employing any or all known medical screening techniques, including proper analytical measures and any necessary treatments to remove any substantial risks of infection.

Human blood is a complex chemical system containing mostly water, a wide variety of proteins, inorganic salts, organic metabolites, and cellular material, including white blood cells, red blood cells and platelets. Blood plasma which can be separated out from whole blood by, for example, centrifugation as described above, generally comprises water, a substantial amount of those proteins and the other blood constituents, except for the cellular materials. Blood plasma can be further separated into a portion which contains a substantial amount of those proteins (herein "the protein portion") and another component containing water and other plasma constituents, by denaturing the proteins or otherwise causing their precipitation (via e.g., pH control, derivatization, solvent precipitation, ammonium sulfate precipitation, etc., as described, for example, in Putnam, F. W., *The Plasma Proteins*, vol. 1, chapter 2 (1960)). The protein portion of the blood plasma generally contains substantially all of the plasma proteins present in blood including serum albumin, very low-density lipoproteins (VLDL's), low-density lipoproteins (LDL's), high-density lipoproteins (HDL's), many different immunoglobulins, fibrinogen, prothrombin, transferrin and other transport proteins.

The protein portion of the blood plasma is cross-linked in accordance with the present invention. The protein portion of the blood plasma can be cross-linked with, for example, chemical reagents or enzymes, or by processes including dehydration and heating, the application of high pressure via the use of, for example, a Parr bomb apparatus, or by ultra-violet irradiation with or without initiators. Cross-linking agents which are especially suitable for use in the present invention include those described in chapters 2 and 6 of Shan Wong, *Chemistry of Protein Conjugation and Cross-Linking*, (1991), the entire contents of which are herein incorporated by reference.

In a preferred embodiment in accordance with the present invention, the protein portion is cross-linked with a zero-length cross-linking agent. Zero-length cross-linking agents are a class of compounds which can induce the direct joining of, and create stable bonds between, two intrinsic chemical moieties of one or more polypeptide chains, without the introduction of any extrinsic matter. Thus, it should be understood that any cross-linking agent which does not introduce extrinsic matter into the cross-linked protein-portion is to be considered a zero-length cross-linking agent, regardless of any particular term used to describe or identify the cross-linking agent, Zero-length cross-linking agents can catalyze, for example, (1) the formation of disulfide bonds between two thiol moieties, (2) the information of ester linkages between hydroxyl and carboxyl moieties, or (3) the formation of amide bonds between carboxyl and primary amino moieties.

Zero-length cross-linking agents which may be used in the present invention include, but are not limited to, carbodiimides, isoxazolinium compounds, chloroformates, carbonyldiimidazoles, N-carbalkoxy-dihydroquinolines, tetranitromethane, potassium nitrosyldisulfonate, and diethylpyrocarbonate. The preferred zero-length cross-linking agents are carbodiimides, most preferably 1-ethyl-3-(3-dimethylaminopropyl) carbodiimide (hereinafter "EDAC"). Carbodiimides are believed to form stable amide bonds between lysine amino acid residues and either glutamate or aspartate amino acid residues.

The extent of cross-linking among the proteins of the protein portion of the blood plasma may be controlled by adjusting several factors including the amount and type of cross-linking agent used, the reaction temperature and the reaction time. Competing reactions such as the hydrolysis of some carbodiimides, which can affect the extent of crosslinking, can also be controlled by adjusting temperature, pH and buffer concentration. Generally, a molar excess of cross-linking agent is used. In the case of EDAC, for example, a seven-fold molar excess or greater is preferably used in the cross-linking reaction. The molar excess being based on molar equivalents of EDAC to molar equivalents of aspartic acid/glutamic acid residues in a protein portion, assuming for the purposes of the calculation that the entire protein portion is albumin (actually~60% albumin). A protein portion of a blood plasma sample can be reacted with an excess of EDAC to form a cross-linked, blood plasma protein product in accordance with the present invention, wherein a substantial amount of glutamate and aspartate residues are cross-linked with lysine residues. The zero-length cross-linked, blood plasma proteins in accordance with the present invention preferably contain at least one amide cross-link. More preferably, they contain at least one amide cross-link which is a lysine-glutamate amide bond or a lysine-aspartate amide bond. Most preferably, an excess of a carbodiimide will result in zero-length cross-linked, blood plasma proteins with essentially all glutamate and/or aspartate residues linked to lysine residues through an amide bond. As used in this context, "essentially all" is understood to mean that at least about 95% of all available lysine residues have formed an amide bond cross-link with carboxylic side chain residues.

Injectable materials in accordance with the present invention generally comprise cross-linked blood plasma proteins as described above, a physiologically acceptable fluid and optionally an anesthetic compound. Typically, the cross-linked, blood plasma proteins comprise from about 1% to about 10% by weight of the injectable material. More preferably, the cross-linked, blood plasma proteins comprise from about 3% to about 7% by weight of the material, and most preferably, from about 5.5. % to about 6.5% by weight of the material, all percentage values being based on dry protein weight.

Physiologically acceptable fluids which can be carriers or vehicles for the injectable materials of the present invention include, for example, normal saline, dextrose solutions, buffered saline including phosphate buffered saline solutions, balanced salt solutions, and any other inactive injectable vehicles. Incorporation of the cross-linked blood plasma protein materials of the present invention into such physiologically acceptable fluids provides an injectable material with a viscosity that upon injection as a soft tissue augmentation material, provides an aesthetically pleasing appearance and natural feel. Some portion of any physiologically acceptable fluid incorporated into the injectable materials in accordance with the present invention may be absorbed by the body after injection. Thus, an amount of injectable material greater than the volume of the skin defect to be augmented may need to be injected into the patient, as described below in relation to injection procedures. The physiologically acceptable fluids generally comprise from about 99% to about 90% by weight of the injectable material of the present invention. Preferably, the physiologically acceptable solutions comprise from about 97% to about 93% by weight of the material, and most preferably, in from about 94.5% to about 95.5% by weight of the material.

Anesthetic compounds may be included in the injectable materials of the present invention in order to alleviate any pain associated with the injection of the materials of the present invention. Such anesthetic compounds include, for example, lidocaine, procaine, tetracaine, prilocalne, mepivacaine, etidocaine, bupivacaine, and other amide and ester anesthetics. The anesthetic compound can be present in the injectable material in an amount up to about 2% by weight of the material. Preferably the injectable materials in accordance with the present invention include an anesthetic compound in an amount from about 0.25% to about 2% by weight of the material.

Furthermore, the injectable materials for soft tissue augmentation in accordance with the present invention may also contain one or more of a wide variety of additional components. For example, the materials comprising cross-linked blood plasma proteins may also include vitamins, growth factors, enzyme inhibitors such as chelators, as well as any other additive which may enhance the material's ability to resist proteolytic cleavage or otherwise inhibit degradation of the material, without causing an adverse reaction in the patient. Examples of such additives include vitamin C, basic fibroblast growth factor, EDTA (added after cross-linking is complete), edetate calcium disodium, desferoxamine mesylate, penicillamine, trientine HCl dimercaptosuccinic acid.

In preferred embodiments of the present invention, the method for preparing injectable materials for soft tissue augmentation may further comprise any one or more of the following: subjecting the cross-linked blood plasma protein product to dialysis; autoclaving the dialyzed product; homogenizing the autoclaved protein product; and loading the protein product into a syringe for storage or use.

Additionally, it is preferred in the method for preparing injectable materials for soft tissue augmentation in accordance with the present invention, that the providing of the protein portion of the blood plasma sample comprises providing a blood plasma sample and separating out the protein portion. A preferred method of separation includes the precipitation of the protein portion of the blood plasma sample.

In an even more preferred embodiment of the present invention, the step of precipitating the protein portion of the blood plasma sample is performed by acidifying the blood plasma sample and mixing the acidified blood plasma sample with a nonaqueous solvent. Preferably, the blood plasma sample is acidified to a pH of approximately 4.5. Addition of an acid solution can be used to accomplish this step. Acids such as hydrochloric, sulfuric, perchloric, nitric, phosphoric, acetic and others can be used. The specific acid used is in no way critical and any excess can later be neutralized by the addition of a base in any event. The pH is adjusted to be near the isoelectric point of serum albumin, a major protein present in blood plasma. By nearing the isoelectric point of serum albumin, precipitation of a greater proportion of the proteins may be attainable. The nonaqueous solvent, which is mixed with the acidified blood plasma sample, can be any solvent which contains minimal water, and is preferably water-free. Water should be avoided prior to cross-linking as it can hydrolyze certain cross-linking agents and thereby decrease their ability to cross-link. Anhydrous alkanols are preferred solvents and anhydrous ethanol is especially preferred due to its ready availability, boiling point, dielectric constant and dermatological acceptability. The acidified blood plasma sample is preferably added to a vessel (e.g., beaker, tube, flask, etc.) containing a nonaqueous solvent. The volume of nonaqueous solvent to be mixed with the acidified blood plasma sample is preferably greater than the volume of acidified blood plasma sample for dilution purposes, but the specific amount is not critical.

The method of the present invention preferably comprises the step of preheating the nonaqueous solvent prior to the addition of the acidified blood plasma sample. It is also preferable in accordance with the method of the present invention, that the method further comprise maintaining the nonaqueous solvent at as high a temperature as possible but below the boiling point of the nonaqueous solvent during the addition of the acidified blood plasma sample. In the case of anhydrous ethanol, a temperature range of 70° to 78° C. is appropriate, with 74° C. being a preferred temperature. By elevating the temperature at which the proteins are precipitated, the resulting particle size of the precipitated proteins can be reduced. Smaller particle sizes allow for injection using higher gauge (smaller inner diameter) needles. The nonaqueous solvent/acidified blood plasma sample/precipitated blood plasma proteins mixture can be reacted with a cross-linking agent as is, or some amount of the liquid in the mixture may be removed, for example, by decantation or drying. It is not necessary to remove any of the nonaqueous solvent or acid at this point. It is only necessary to minimize the presence of water in the mixture as water can hydrolyze certain crosslinking agents such as carbodiimides.

The cross-linking agent can be mixed with the precipitated protein portion in an amount of at least about 0.1% by weight/volume ("w/v") and is preferably present in an amount of at least about 1% w/v, and most preferably in an amount of at least about 2% w/v. In a preferred embodiment of the present invention, EDAC is added in an amount of from about 2.0% w/v to about 3.0% w/v. The reaction with the cross-linking agent is preferably carried out at an elevated temperature in a range of from about 40° C. to about 60° C., and preferably from about 45° C. to about 55° C. Cross-linking may be carried out for virtually any amount of time, although at least one hour is preferred. More preferably, cross-linking is carried out over the course of from about 4 hours to about 6 hours, in order to drive the cross-linking reaction as far towards completion as possible. Temperature, time and amount of cross-linking agent are all important to the extent of cross-linking. While temperature helps to increase the rate of reaction, and longer times may allow for substantial completion of the reaction, excess (molar) cross-linking agent is also helpful, especially in the case of carbodiimides. While carbodiimides do not generally become incorporated into the resulting cross-linked amide bond, they are believed to be altered during the cross-linking reactions (becoming urea derivatives), and thus lose their cross-linking ability. Therefore, it is advantageous to add a molar excess of carbodiimide cross-linking agent in order to ensure that essentially all glutamate and aspartate residues are linked to lysine residues through an amide bond.

Once the plasma proteins have been allowed to react with the cross-linking agent, the plasma can be neutralized with a base such as sodium bicarbonate or sodium hydroxide. Adjustment of the pH to an approximately neutral value (~7.0) generally reduces any potential irritation that could be caused by acidic compositions. The particular base to be used is not critical. Additionally, a substance can be added to quench any excess cross-linking agent. For example, in the case of EDAC, glycine, hydroxylamine, or any other amine-containing compound can be added. Also, β-mercaptoethanol can be added to quench any excess EDAC. No particular quenching agent is preferred, but glycine is commonly used based on convenience. Suitable quenching agents generally provide unbound reactive groups which are usually attacked by the cross-linking agent, and therefore are correspondingly chosen based on the cross-linking agent selected.

The resulting cross-linked, blood plasma protein product, which can be in the form of a suspension of cross-linked proteins in a mixture of solvents including alkanol, acid, base, quenching agent, etc., can be subjected to a variety of post cross-linking treatments including rinsing, dialysis, autoclaving and homogenization.

Rinsing should be performed regardless of any subsequent sterilization and purification. Rinsing can be accomplished by washing with an ethanol/water mixture, which may be, for example, 50/50, spinning and decanting the wash fluid. This may be repeated as many times as desired and followed with at least one or more pure water rinses.

It is preferable to subject the protein product to dialysis for an extended period of time for purification purposes. Preferably, the product is dialyzed for a period of at least 8 weeks. The extended period of dialysis may reduce potential irritation which could be caused by any remaining cross-linking agent present in micromolar concentrations. Dialysis can be performed using known dialysis equipment in accordance with known dialysis procedures.

The purified product can then be sterilized by autoclaving. Autoclaving can be accomplished using known equipment. The material prepared in accordance with the present invention is preferably autoclaved for approximately 45 minutes on a liquid cycle (~140° C.) and allowed to cool to room temperature.

The product can be homogenized by passing the product through successively smaller needles (i.e., increasing gauge). Particle size homogenization can be accomplished by passing the cross-linked blood plasma product prepared in accordance with the present invention through successively higher gauge needles. It is preferable that the material finally be passed through a high gauge needle, for example, a 27G or 30G needle (~190 μm and ~150 μm internal diameters, respectively). Alternatively, automated methods involving large scale/laboratory-sized machines designed for the homogenization and grinding of samples can be used.

Cross-linked blood plasma proteins can be injected through needles into intradermal compartments of a patient's skin to decrease the visibility of defects in the skin. In a preferred embodiment in accordance with the present invention, a method for augmenting a patient's soft tissue in the area of a surface skin defect includes injecting a cross-linked blood plasma protein portion through a high gauge needle into the intradermal compartment of a patient's skin in the area of a defect. Skin defects which can be treated in accordance with the method of the present invention include wrinkles, expression lines, pockmarks, acne scars, etc.

As with any medical procedure, the injection of materials for soft tissue augmentation in accordance with the present invention should be practiced by experienced medical professionals, who are knowledgeable about soft tissue augmentation.

The type of defect to be corrected often determines the gauge of needle to be used. The finer, or narrower, the defect the higher the gauge of the needle should be. This corresponds to a need for less material in augmenting smaller tissue defects. The location of injection should be superficial and is preferably an intradermal compartment of the skin located between the epidermal and dermal layers of the skin. Fluid loss, which usually occurs within the first 24 to 48 hours after injection, can be addressed by injecting from about 25% to about 50% more material than the skin defect requires (i.e., over-correction).

The present invention will now be illustrated in more detail by reference to the following, non-limiting examples.

PREPARATION EXAMPLE 1

An injectable material in accordance with the present invention was prepared as follows. Venous blood was withdrawn from a patient using a standard syringe method. The blood was contained in two collection tubes having an 8.5 mL draw capacity with glycerated stoppers and each containing 1.5 mL of an aqueous solution which included trisodium citrate at 22 g/l, citric acid at 8 g/l and dextrose at 25 g/l. The collection tubes, which did not contain any EDTA, were VACUTAINER® evacuated specimen tubes having HEMOGARD™ closures having shielded stoppers and outer rims. These tubes can be obtained from Becton-Dickinson or distributors.

The tubes containing the withdrawn blood were centrifuged at room temperature for 10 minutes at a speed of 1500 rpm (654 relative centrifugal force ("RCF")), using a Sorvall RC3C centrifuge in an H6000A swinging bucket rotor to separate the plasma from the cellular materials. Approximately 10 mL of plasma was removed from the tubes using a sterilized pipette and placed in small sterilized beaker.

700 μL of 1 N hydrochloric acid were added to the plasma. The acidified solution was swirled by hand and drawn up into a 10 cc syringe. The pH of the acidified plasma solution was approximately 4.5. Separately in a sterile bottle with a cap, 100 mL of pure, non-denatured ethanol were heated to approximately 72° C. with constant stirring using a stir bar.

A fine gauge (27G) needle was attached to the syringe containing the acidified plasma, and the plasma was slowly added to the ethanol with continued stirring. The temperature was maintained throughout the addition. The bottle was then capped, and the heating and stirring were continued for approximately 10 minutes.

2.2 grams of pure EDAC were then added, corresponding to 2% EDAC by weight based on total volume (w/v). After the EDAC was added, the bottle was capped and allowed to stand with lower heat (~medium setting on most standard hot plates) and continuous stirring for approximately 4.5 hours. With the heat source turned off and with continued stirring, 1.4 mL of 5% sodium bicarbonate were added to neutralize the hydrochloric acid. 2 grams of glycine were also added to quench any excess EDAC. The mixture was continuously stirred overnight at room temperature for approximately 16–18 hours.

The contents of the bottle were then poured into two 50 mL conical tubes. The tubes were then centrifuged at 1200 rpm for about 8 minutes. The supernatant was carefully decanted. The remaining centrifuged product was rinsed with a 50% solution of ethanol in water, centrifuged and decanted again. The rinse was repeated three times using milli-Q water.

The cross-linked, blood plasma protein product thus obtained was then poured into a dialysis apparatus and treated for 8 weeks at 4° C. The water was changed every other day and 0.1% benzyl alcohol was used as a preservative, although any non-toxic, antimicrobial preservative could be used. The material was then autoclaved for 45 minutes on liquid cycle and allowed to cool. The contents were then transferred to a 50 mL conical tube and centrifuged once again at 1200 rpm for about 10 minutes, and the supernatant decanted, yielding approximately 10 mL of cross-linked blood plasma proteins.

40 mL of sterilized, phosphate-buffered saline solution with a pH of 7.4 and 0.5 mL of a 50% sterile lidocaine HCl stock solution (to yield a final concentration of 0.5%) were mixed with the product and vortexed. The contents were again centrifuged at 1200 rpm for about 10 minutes and the supernatant carefully decanted, leaving a residual amount of approximately 1 mL of lidocaine/phosphate-buffered saline solution in the tube to facilitate the subsequent homogenization.

The centrifuged product was placed in a sterilized 10 cc syringe and a low gauge needle (19G) was attached. The product was injected into the barrel of another sterilized 10 cc syringe to which a higher gauge needle (23G) was attached. The product was then injected into the barrel of the first syringe and the 19G needle was changed to a 25G needle and the product was injected into the second syringe as before. Using the syringe plunger, any trapped air was eliminated and the product was loaded into 1 cc syringes, capped, labeled and stored at 4° C.

PREPARATION EXAMPLE 2

An injectable material for soft tissue augmentation was prepared in accordance with Example 1 except that 1.1 grams of pure EDAC were added, corresponding to 1% EDAC by w/v.

PREPARATION EXAMPLE 3

An injectable material for soft tissue augmentation was prepared in accordance with Example 1 except that 0.11 grams of pure EDAC were added, corresponding to 0.1% EDAC by w/v.

PREPARATION EXAMPLE 4

An injectable material for soft tissue augmentation was prepared in accordance with Example 1 except that 4.4 grams of pure EDAC were added, corresponding to 4.0% EDAC by w/v.

PREPARATION EXAMPLE 5

An injectable material for soft tissue augmentation was prepared in accordance with Example 1 except that 5.5 grams of pure EDAC were added, corresponding to 5.0% EDAC by w/v.

COMPARATIVE PREPARATION EXAMPLE 1

An injectable material for soft tissue augmentation was prepared using autologous blood plasma which was collected in an ordinary EDTA containing vessel. Vitamin C (0.2% sodium ascorbate) was added to the blood plasma. The plasma was then heat gelled in 1 cc syringes for 5 minutes at 70° C. in a hot water bath and for 2 minutes at 95° C. The syringes were then allowed to cool to room temperature. No cross-linking was performed.

USE EXAMPLE 1

Several hairless mice received injections of the material for soft tissue augmentation prepared in Preparation Example 1. Each hairless mouse was lightly anesthetized via METOFANE™ methoxyflueane inhalation anesthetic (available from Schering-Plough Corp., Union, N.J.) inhalation. Each mouse then received four to six intradermal subcutaneous injections using 27G needles. Volume per injection site was approximately 0.1 cc.

Figure 2:
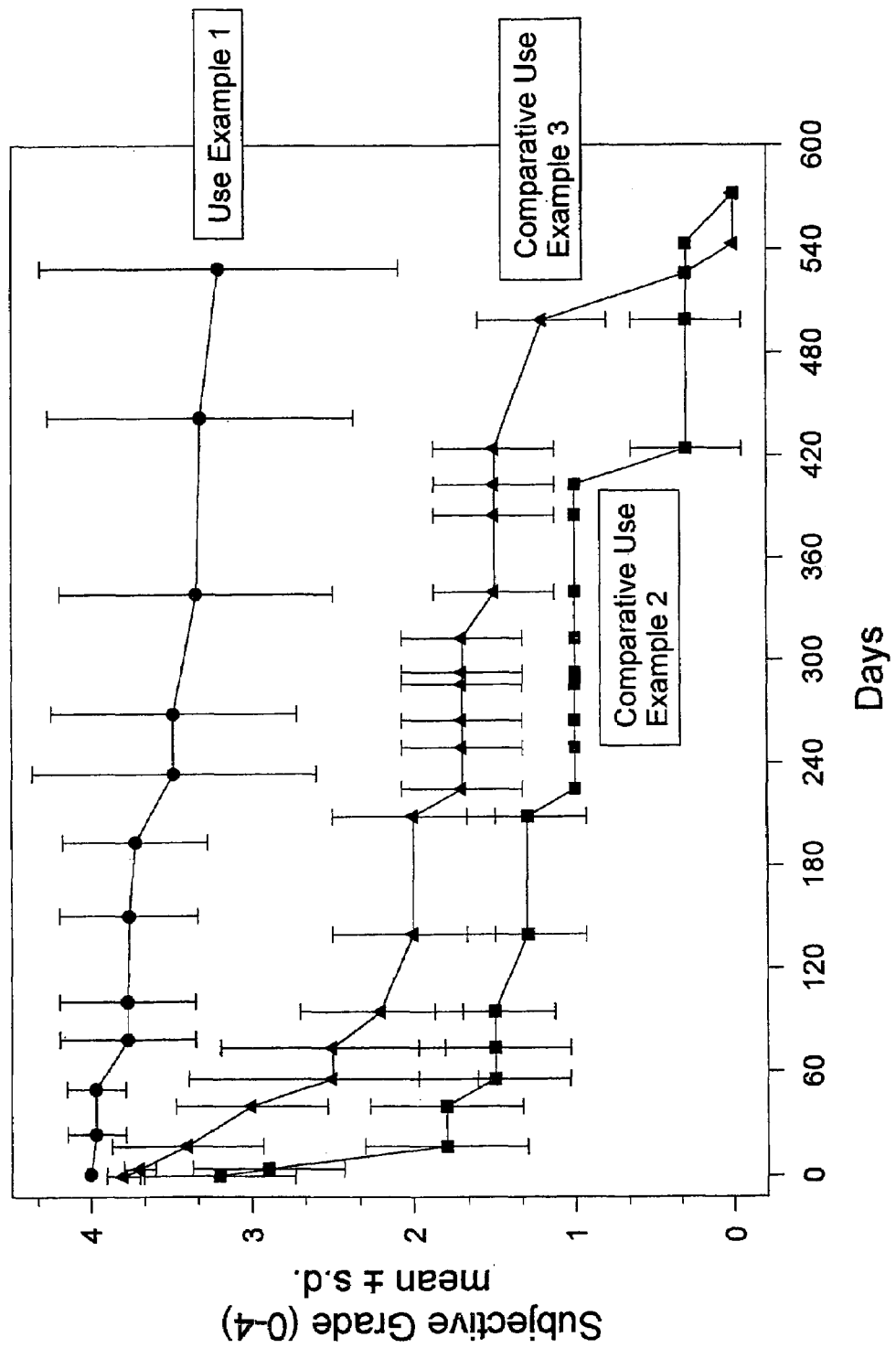
FIG. 2 is a graphical representation over time as measured in days of the subjective effect of in vivo proteolytic degradation and phagocytosis (biodegradation) of injectable materials as used in Use Example 1 and Comparative Use Examples 2 and 3.
Figure 3:
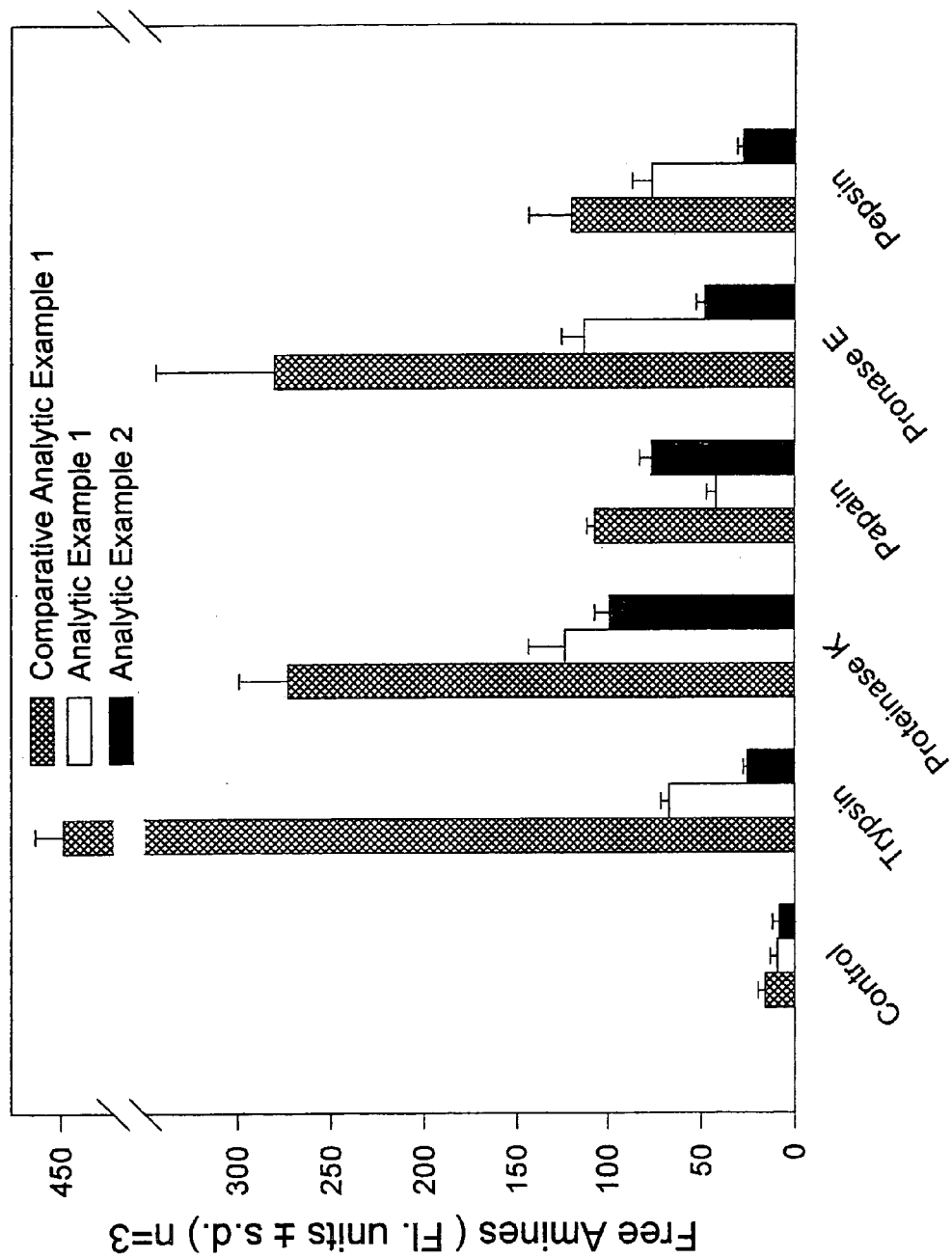
FIG. 3 is a graphical representation of the quantitative effect of in vitro proteolytic degradation on injectable materials prepared in accordance with Preparation Examples 1 and 2 and Comparative Preparation Example 1, as measured by florescence assay of free amines present, as described in Analytic Examples 1 and 2 and Comparative Analytic Example 1.

Each injection site was examined at weekly to monthly intervals for any signs of irritation (erythema, ulceration, etc.) and assigned a grade based on visual inspection. Initial injection volume was designated a grade of 4. Diminishing appearances received values of 3, 2, 1, and 0. Conducting the evaluations using hairless mice allows for easy inspection of the injection sites. Two injection sites eventually exhibited erythema and ulceration. The results of the evaluation are set forth in Table I below and are shown graphically in FIGS. 1 and 2.

COMPARATIVE USE EXAMPLE 1

A separate group of several hairless mice received injections (192 injections total) in accordance with Preparation Example 3, except that the material of Comparative Preparation Example 1 was used. Eight injection sites eventually exhibited erythema and ulceration. The results of the evaluation are set forth in Table I below and are shown graphically in FIG. 1.

COMPARATIVE USE EXAMPLE 2

A separate group of several hairless mice received injections (nine injections total) in accordance with Use Example 1, except that a bovine collagen injectable material marketed as ZYDERM®, a collagen implant composed of highly purified, bovine dermal collagen dispersed in phosphate-buffered physiologic saline containing 0.3% lidocaine by Collagen Corp., of Palo Alto, Calif., was used. This material exhibited a gradual reduction in volume over 550 days. The material was not visible upon autopsy after natural death of the mice. The results of the evaluation are set forth in Table I below and are shown graphically in FIG. 2.

COMPARATIVE USE EXAMPLE 3

A separate group of several hairless mice received injections (nine injections total) in accordance with Use Example 1, except that at a glutaraldehyde cross-linked, bovine collagen injectable material dispersed in a phosphate-buffered physiological saline containing 0.3% lidocaine marketed as ZYPLAST® collagen by Collagen Corp., of Palo Alto, Calif., was used. This material also exhibited a gradual reduction in volume over 550 days. The material was also not visible upon autopsy after natural death of the mice. After approximately one-year, two of the nine injection sites showed evidence of inflammation with low-grade erythema. The results of the evaluation are set forth in Table I below and are shown graphically in FIG. 2.

TABLE I

| Use Example 1 | | Comparative Use Example 1 | | Comparative Use Example 2 | | Comparative Use Example 3 | |
| --- | --- | --- | --- | --- | --- | --- | --- |
| Days | Avg. Rating | Days | Avg. Rating | Days | Avg. Rating | Days | Avg. Rating |
| 1 | 4.000 | 1 | 3.916 | 1 | 3.20 | 1 | 3.80 |
| 24 | 3.967 | 6 | 3.898 | 4 | 2.90 | 4 | 3.70 |
| 50 | 3.967 | 30 | 3.169 | 17 | 1.80 | 17 | 3.40 |
| 79 | 3.770 | 49 | 3.108 | 40 | 1.80 | 40 | 3.00 |
| 101 | 3.770 | 109 | 1.191 | 56 | 1.50 | 56 | 2.50 |
| 151 | 3.762 | 170 | 1.173 | 74 | 1.50 | 74 | 2.50 |
| 194 | 3.723 | 235 | 1.019 | 95 | 1.50 | 95 | 2.20 |
| 234 | 3.483 | 257 | 1.185 | 140 | 1.30 | 140 | 2.00 |

TABLE I-continued

| Use Example 1 | | Comparative Use Example 1 | | Comparative Use Example 2 | | Comparative Use Example 3 | |
|---|---|---|---|---|---|---|---|
| Days | Avg. Rating | Days | Avg. Rating | Days | Avg. Rating | Days | Avg. Rating |
| 269 | 3.482 | 292 | 1.175 | 209 | 1.00 | 209 | 2.00 |
| 339 | 3.340 | 369 | 1.205 | 225 | 1.00 | 225 | 1.70 |
| 442 | 3.313 | 418 | 1.000 | 249 | 1.00 | 249 | 1.70 |
| 529 | 3.200 | | | 265 | 1.00 | 265 | 1.70 |
| 656 | 3.091 | | | 286 | 1.00 | 286 | 1.70 |
| 693 | 3.019 | | | 293 | 1.00 | 293 | 1.70 |
| | | | | 313 | 1.00 | 313 | 1.70 |
| | | | | 340 | 1.00 | 340 | 1.50 |
| | | | | 385 | 1.00 | 385 | 1.50 |
| | | | | 403 | 1.00 | 403 | 1.50 |
| | | | | 424 | 0.30 | 424 | 1.50 |
| | | | | 499 | 0.30 | 499 | 1.20 |
| | | | | 526 | 0.30 | 526 | 0.30 |

ANALYTIC EXAMPLE 1

The quantitative effectiveness of the cross-linking in accordance with the present invention with respect to increasing the material's resistance to proteolytic attack was measured by the in-vitro susceptibility to several different proteinases. The proteinases against which proteolytic resistances were tested include trypsin, proteinase K, papain, pronase E, pepsin, cathespin G and leucine aminopeptidase. The in-vitro susceptibility test used in accordance with this example was adapted from the free amine assay disclosed in Udenfriend, et al., "Fluorescamine: A Reagent for Assay of Amino Acids, Peptides, Proteins, and Primary Amines in the Picomole Range", SCIENCE, Vol. 178, pp. 871–2 (November 1972), the entire contents of which are herein incorporated by reference.

250 milligrams of the material prepared in accordance with Preparation Example 1 were injected into each of seven glass test tubes (6×50 mm). Then, 250 μL of a proteinase (a different one in each tube) in the appropriate concentration, based on manufacturer-indicated enzyme activities, were added to each tube. The tubes were then centrifuged for ten minutes at 1000×G (times gravity) and then incubated at 37° C. After 30 minutes, 150 μL of the supernatant of each tube (alternatively 10 μL diluted with 140 μL of buffer solution) was removed to a 1.5 mL Eppendorf centrifuge tube. The proteins in each 1.5 mL tube were precipitated with 38 μL of 100% trichloroacetic ("TCA") over ten minutes while cooling with ice. The tubes were then centrifuged at 12000×G in an Eppendorf Model 5415C microcentrifuge for ten minutes. 150 μL of each resulting supernatant was transferred to a glass culture tube and combined with 1.49 mL of 0.2 M boric acid resulting in a final pH of approximately 9. After mixing, 0.5 mL of fluorescamine (0.015% in HPLC grade acetone) was added to each tube, and the tubes were vortexed vigorously for ten seconds.

Fluorescence was then measured using a Foci Fluorometer (obtained from Optical Technology Devices, Inc., Elmsford, N.Y.) with filters corresponding to 390 nm excitation and 475 nm emission. Blanks with no protein, as well as each sample were run in triplicate. A linear relationship exists between glycine concentration and fluorescence, allowing for enzyme activities to be calculated based on comparisons to the standard curve for known concentrations of glycine.

All of the proteinases tested had significantly reduced cleaving abilities as evidenced by the decreased amount of free amine present. The results of the free amine assay in accordance with this example are set forth below in Table II. As can be seen from the data, cross-linking of blood-plasma proteins causes a substantial reduction in proteolytic cleavage.

ANALYTIC EXAMPLE 2

The material prepared in Preparation Example 2 was subjected to the in vitro susceptibility test of Analytic Example 1. The results are set forth below in Table II. As can be seen from the data, the material prepared in accordance with Preparation Example 2, which used more cross-linking agent to effect a greater extent of cross-linking, had even lower susceptibility to proteolytic cleavage.

COMPARATIVE ANALYTIC EXAMPLE 1

The material prepared in Comparative Preparation Example 1 was subjected to the in vitro susceptibility test of Analytic Example 1. The results are set forth below in Table II. As can be seen from the data, the material prepared in accordance with Comparative Preparation Example 1 had significantly less resistance to proteolytic cleavage.

TABLE II

| | Analytic Example 1 (Preparation Example 1) | | | Analytic Example 2 (Preparation Example 2) | | | Comparative Analytic Example 1 (Comparative Preparation Example 1) | | |
|---|---|---|---|---|---|---|---|---|---|
| Proteinase Enzyme Name | Free Amines (μg) (glycine equiv.'s) | μg G.E./ mg protease/ h | μg G.E./ u/h | Free Amines (μg) (glycine equiv.'s) | μg G.E./ mg protease/ h | μg G.E./ u/h | Free Amines (μg) (glycine equiv.'s) | μg G.E./ mg protease/ h | μg G.E./ u/h |
| Trypsin | 6 | 60 | 0.48 | 1 | 10 | 0.08 | 23 | 230 | 1.84 |
| Proteinase K | 50 | 50 | 4.17 | 34 | 34 | 2.83 | 88 | 88 | 7.33 |
| Papain | 10 | 10 | 0.67 | 20 | 20 | 1.33 | 14 | 14 | 0.93 |
| Pronase E | 24 | 24 | N/A | 6 | 6 | N/A | 75 | 75 | N/A |
| Pepsin | 10 | 10 | 0.0034 | 2.5 | 2.5 | 0.00 | 20 | 20 | 0.01 |
| Cathespin G | 0 | 0 | 0.00 | — | — | — | 0.75 | 75 | 1500.00 |
| LAP* | 0.5 | 5 | 0.42 | — | — | — | 0.75 | 7.5 | 0.63 |

*Leucine aminopeptidase

ANALYTICAL EXAMPLE 3

Several hairless mice received injections in accordance with Use Example 1, using the injectable material prepared in accordance with Preparation Example 1. Euthanasia by $CO_2$ inhalation and removal of injection sites, including surrounding skin and underlying tissue, were performed 24 hours, 72 hours, 7 days, 14 days, 30 days, 6 months and 18 months post-injection. The removed injection sites were fixed in buffered formalin, paraffin embedded, and cut into 5 μm sections. Each section was stained with hematoxylin and eosin (HE) and examined at 60× and 100× magnification. Injection sites removed at 24 hours and 72 hours post injection showed expected minor inflammatory response. Injection sites removed at 7 days, 14 days and 30 days post injection, showed the formation of a fibrous layer around the injected material. Injection sites removed at 6 and 18 months post injection showed no inflammation in the vicinity of the injected material.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of augmenting a soft tissue defect in a skin area of a mammal, the method comprising intradermally injecting into the skin of the mammal a material comprising cross-linked, blood plasma proteins, wherein the cross-linkages comprise at least one intermolecular amide bond.

2. The method of claim 1, wherein the cross-linkages are zero-length cross linkages.

3. The method of claim 1, wherein the at least one amide bond is selected from a lysine-glutamate amide bond and a lysine-aspartate amide bond.

4. The material of claim 1, wherein cross-linked blood plasma proteins are present in the material in an amount of about 1% to about 10% by total weight of the injectable material.

5. The material of claim 1, wherein the material further comprises a component selected from the group consisting of an anesthetic compound, a vitamin, a growth factor, and an enzyme inhibitor.

6. The method of claim 1, wherein the intradermally-injected material is prepared by a method comprising forming intermolecular cross-linkages between and among blood plasma proteins.

7. The method of claim 1, wherein the blood plasma proteins are autologous to the mammal into which they are injected.

8. The material of claim 1, wherein the material further comprises a physiologically acceptable fluid.

9. The material of claim 8, wherein the physiologically acceptable fluid is present in the material in an amount of about 99% to about 90% by weight of the injectable material.

10. The method of claim 1, wherein the intradermally-injected material is prepared by a method comprising
    (a) obtaining a blood plasma sample from the mammal,
    (b) precipitating a protein portion from the blood plasma sample,
    (c) forming intermolecular cross-linkages between and among blood plasma proteins of the protein portion, wherein the cross-linkages comprise at least one amide bond.

11. The method of claim 10, further comprising the subsequent step of dialyzing the cross-linked blood plasma proteins.

12. The method of claim 10, further comprising the subsequent step of autoclaving the cross-linked blood plasma proteins.

13. The method of claim 10, wherein step (b) comprises acidifying the blood plasma sample and mixing the acidified blood plasma sample with a nonaqueous solvent.

14. The method of claim 13, wherein the blood plasma sample is acidified to a pH of about 4.5.

15. The method of claim 13, wherein the nonaqueous solvent is an anhydrous alkanol.

16. The method according to claim 13, wherein step (c) comprises mixing the zero-length cross-linking agent with the protein portion in an amount of at least about 0.1% by volume of the protein portion.

17. The method of claim 10, wherein step (c) is the forming cross-linkages uses a zero-length cross-linking agent.

18. The method of claim 17, wherein the zero-length cross-linking agent is selected from the group consisting of carbodiimides, isoxazolinium compounds, chloroformates, carbonyldiimidazoles, N-carbalkoxydihydroquinolines, tetranitromethane, potassium nitrosyldisulfonate, and diethylpyrocarbonate.

19. The method according to claim 17, wherein the zero-length cross-linking agent comprises 1-ethyl-3-(3-dimethylaminopropyl)carbodiimide.

* * * * *